US009833352B2

(12) United States Patent
Maidl et al.

(10) Patent No.: US 9,833,352 B2
(45) Date of Patent: Dec. 5, 2017

(54) OSTOMY DEVICES (75) Inventors: Laurie J. Maidl, Rochester, MN (US); William A. Faubion, Rochester, MN (US); Eric J. Dozois, Rochester, MN (US); Troy J. Ziegler, Plymouth, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/592,986

(22) Filed: Aug. 23, 2012

(65) Prior Publication Data

US 2013/0053802 A1 Feb. 28, 2013

Related U.S. Application Data

(60) Provisional application No. 61/526,563, filed on Aug. 23, 2011.

(51) Int. Cl.
  *A61F 5/441* (2006.01)
  *A61F 5/445* (2006.01)
  *A61F 5/44* (2006.01)

(52) U.S. Cl.
  CPC .................................. *A61F 5/445* (2013.01)

(58) Field of Classification Search
  CPC ........... A61F 5/445; A61F 5/44; A61F 5/4405
  USPC ....................................................... 604/332
  See application file for complete search history.

(56) References Cited

U.S. PATENT DOCUMENTS

| | | | |
|---|---|---|---|
| 2,875,451 A | | 3/1959 | Stegeman et al. |
| 3,724,461 A | | 4/1973 | Eisenberg |
| 3,825,005 A | | 7/1974 | Fenton |
| 3,952,726 A | | 4/1976 | Hennig |
| 4,211,224 A | | 7/1980 | Kubach et al. |
| 4,338,937 A | | 7/1982 | Lerman |
| 4,351,322 A | | 9/1982 | Prager |
| 4,367,732 A | | 1/1983 | Poulsen et al. |
| 4,403,991 A | | 9/1983 | Hill |
| 4,411,659 A | * | 10/1983 | Jensen et al. ................. 604/332 |
| 4,451,490 A | | 5/1984 | Silverman et al. |
| 4,490,145 A | * | 12/1984 | Campbell ..................... 604/333 |
| 4,596,566 A | | 6/1986 | Kay |
| 4,755,177 A | | 7/1988 | Hill |
| 4,834,731 A | | 5/1989 | Nowak et al. |
| 5,051,259 A | | 9/1991 | Olsen et al. |
| 5,074,851 A | | 12/1991 | Plass et al. |
| 5,085,652 A | * | 2/1992 | Johnsen et al. .............. 604/333 |

(Continued)

FOREIGN PATENT DOCUMENTS

| EP | 64044 B1 | 2/1986 |
|---|---|---|
| EP | 868892 A1 | 10/1998 |

(Continued)

OTHER PUBLICATIONS

U.S. Appl. No. 61/521,605, filed Aug. 9, 2011, 30 pages.

(Continued)

*Primary Examiner* — Philip R Wiest
*Assistant Examiner* — Sara Sass
(74) *Attorney, Agent, or Firm* — Fish & Richardson P.C.

(57) ABSTRACT

This document provides methods and materials related to ostomy devices. For example, ostomy bags or pouches that can be used to collect discharge from a temporary or permanent ostomy opening are provided.

14 Claims, 4 Drawing Sheets

(56) References Cited

U.S. PATENT DOCUMENTS

| | | | |
|---|---|---|---|
| 5,125,133 A | 6/1992 | Morrison | |
| 5,167,650 A | 12/1992 | Johnsen et al. | |
| 5,250,042 A * | 10/1993 | Torgalkar et al. | 604/333 |
| 5,306,264 A * | 4/1994 | Ferguson et al. | 604/333 |
| 5,348,546 A * | 9/1994 | Norton | 604/333 |
| 5,369,130 A | 11/1994 | Numata | |
| 5,401,264 A | 3/1995 | Leise, Jr. | |
| 5,468,235 A | 11/1995 | La Gro | |
| 5,618,276 A | 4/1997 | Leise, Jr. et al. | |
| 5,658,267 A | 8/1997 | Colacello et al. | |
| 5,690,623 A * | 11/1997 | Lenz et al. | 604/333 |
| 5,714,225 A | 2/1998 | Hansen et al. | |
| 5,772,644 A * | 6/1998 | Bark | A61B 10/0096 600/573 |
| 5,800,415 A | 9/1998 | Olsen | |
| 5,947,941 A | 9/1999 | Leise, Jr. et al. | |
| 6,032,831 A | 3/2000 | Gardner et al. | |
| 6,135,986 A * | 10/2000 | Leisner et al. | 604/322 |
| 6,165,159 A | 12/2000 | Blanton | |
| 6,171,594 B1 | 1/2001 | Nielsen | |
| 6,303,700 B1 | 10/2001 | Chen | |
| 6,332,879 B1 | 12/2001 | Nielsen et al. | |
| 6,437,038 B1 | 8/2002 | Chen | |
| 6,451,883 B1 | 9/2002 | Chen et al. | |
| 6,544,241 B2 | 4/2003 | Morton | |
| 6,689,111 B2 | 2/2004 | Mulhauser | |
| 6,709,421 B1 | 3/2004 | Falconer | |
| 6,878,130 B2 | 4/2005 | Fournie | |
| 7,087,041 B2 | 8/2006 | von Dyck | |
| 7,604,622 B2 | 10/2009 | Pedersen et al. | |
| 7,727,205 B2 | 6/2010 | Leisner | |
| 7,765,007 B2 | 7/2010 | Martino | |
| 8,998,862 B2 | 4/2015 | Hanuka | |
| 2002/0077611 A1 | 6/2002 | von Dyck | |
| 2003/0181879 A1 | 9/2003 | Mulhauser | |
| 2003/0236509 A1 | 12/2003 | Silvestrini | |
| 2004/0049837 A1 | 3/2004 | Falconer et al. | |
| 2005/0131360 A1 | 6/2005 | Villefrance et al. | |
| 2009/0157140 A1 | 6/2009 | Martino | |
| 2010/0010460 A1 | 1/2010 | Butler | |
| 2010/0145291 A1 | 6/2010 | Kambara | |
| 2011/0028924 A1 | 2/2011 | Murray | |
| 2011/0040270 A1 | 2/2011 | Ciok et al. | |
| 2011/0060362 A1 | 3/2011 | Patel et al. | |
| 2011/0092929 A1 | 4/2011 | Weig | |
| 2012/0116447 A1 | 5/2012 | Stanley et al. | |
| 2012/0136324 A1 | 5/2012 | Hanuka | |
| 2012/0245519 A1 | 9/2012 | Rotella | |
| 2014/0194843 A1 | 7/2014 | Masters et al. | |
| 2015/0164679 A1 | 6/2015 | Maidl et al. | |

FOREIGN PATENT DOCUMENTS

| | | |
|---|---|---|
| EP | 2407129 B1 | 1/2013 |
| GB | 2139501 A | 11/1984 |
| GB | 2265832 A | 10/1993 |
| WO | WO9101118 A1 | 2/1991 |
| WO | WO9101119 A1 | 2/1991 |
| WO | WO9318725 A1 | 9/1993 |
| WO | WO9418919 A1 | 9/1994 |
| WO | WO0030576 A1 | 6/2000 |
| WO | WO0154632 A1 | 8/2001 |
| WO | WO03065946 A1 | 8/2003 |
| WO | WO2004004612 A1 | 1/2004 |
| WO | WO2010030426 A1 | 3/2010 |
| WO | WO2010060115 A1 | 5/2010 |
| WO | WO2010106039 A1 | 9/2010 |
| WO | WO2013022575 A1 | 2/2013 |

OTHER PUBLICATIONS

Faller et al., "The MIC-KEY," Ostomy Wound Manage., 38(3):50-53, Apr. 1992.

Soliani et al., "Colostomy plug devices: a possible new approach to the problem of incontinence," Dis Colon Rectum., 35(10):969-974, Oct. 1992.

International Search Report and Written Opinion for PCT/US2013/048953, mailed Oct. 2, 2013, 7 pages.

International Preliminary Report on Patentability for PCT/US2013/048953, Jan. 6, 2015, 6 pages.

European Search Report for EP App. No. 13812993.7, mailed Jan. 20, 2016, 6 pages.

Office Action in U.S. Appl. No. 14/412,127, dated Jan. 17, 2017, 25 pages.

\* cited by examiner

FIG. 4B

OSTOMY DEVICES

CROSS REFERENCE TO RELATED APPLICATIONS

This application claims the benefit of U.S. Provisional Application Ser. No. 61/526,563, filed Aug. 23, 2011. The disclosure of the prior application is considered part of (and is incorporated by reference in) the disclosure of this application.

BACKGROUND

1. Technical Field

This document relates to ostomy devices. For example, this document relates to ostomy bags or pouches that can be used to collect discharge from a temporary or permanent ostomy opening.

2. Background Information

Treating some diseases of the digestive or urinary systems can involve removing all or part of a patient's small intestine, colon, rectum, or bladder. In these cases, waste must be rerouted to exit the body of the subject. The rerouting surgery, known as an ostomy, can involve creating an opening in the abdomen wall so that a portion of the intestinal tract can be brought out to the skin level, resulting in what is called a stoma. Three common types of abdominal wall stomas result from, and may be classified as, a colostomy, ileostomy, and urostomy, which involve patients who have had surgery on their the large intestine, small intestine, and urinary bladder, respectively. Typically, a medical prosthetic known as an ostomy pouching system can be used to collect waste from a diverted biological system as it exits a stoma.

SUMMARY

This document provides methods and materials related to ostomy devices. For example, this document provides ostomy bags or pouches that can be used to collect waste material from a temporary or permanent ostomy opening. In some cases, an ostomy bag or pouch provided herein can be used to divide stomal effluent or waste product into a solid fraction and a liquid fraction. As described herein, an ostomy pouch, which divides stomal discharge into a solid fraction and a liquid fraction, can allow ostomy patients to drain the liquid fraction while retaining the solid fraction for future disposal. In some cases, ostomy bags and pouches provided herein can divide stomal effluent into a solid fraction and a liquid fraction, thereby providing improved waste management options for ostomy patients.

In general, one aspect of this document features an ostomy device for collecting stomal effluent. The ostomy device comprises, or consist essentially of, a single compartment and a partition for separating the stomal effluent into a liquid fraction and a solid fraction. The partition can comprise a filtering component.

In another aspect, this document features an ostomy device comprising, or consisting essentially of, at least two compartments and a partition for separating stomal effluent into a liquid fraction and a solid fraction. The device can comprise a first compartment for collection of the solid fraction and a second compartment for collection of the liquid fraction. The first compartment can be partitioned from the second compartment by a filtering component. Each of the at least two compartments can be capable can be emptied independently.

In another aspect, this document features a method for handling waste from a stoma. The method comprises, or consists essentially of, (a) applying an ostomy device to the stoma, (b) allowing the ostomy device to be filled with stomal effluent, and (c) selectively disposing of a liquid fraction of the stomal effluent while retaining a solid fraction of the stomal effluent within the ostomy device. The solid fraction can be retained in a compartment of the ostomy device that is separate from a compartment of the ostomy device that contains a drain opening, wherein the liquid fraction is selectively disposed of through the drain opening.

In another aspect, this document features a method for partitioning a liquid fraction from a solid fraction of an ostomy effluent, wherein the method comprises filtering the ostomy effluent to produce a substantially non-particulate fraction.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

This document provides methods and materials related to ostomy devices. For example, this document provides methods and materials that can be used to collect ostomy waste material. As described herein, ostomy bags or pouches can be configured to divide stomal effluent into a solid fraction and a liquid fraction.

In general, an ostomy bag or pouch or ostomy pouching system can include a mounting plate (e.g., a wafer) and a collection pouch that can be mechanically attached to a mounting plate via an airtight seal. Such ostomy devices can be configured to collect liquid or semisolid waste that exits a stoma. In some cases, an ostomy device can include flat, opposing walls secured together along their edges to define a stomal discharge collection cavity. One of the walls can be provided with an opening to receive a stoma and a connecting flange to secure the bag or pouch to an adhesive barrier placed around the stoma so that waste material discharged through the stoma is received within the collection cavity. At its lower end, an ostomy device can have a discharge opening that can be closed during waste collection, but can be opened for draining the waste material from the pouch after a period of use. In some cases, an ostomy pouch can be designed for single use, in which case it will lack a discharge opening as the entire bag or pouch can be discarded after use.

An ostomy device can be configured as a one or two-piece design. In a one-piece design, an ostomy bag or pouch can interact directly with the skin surrounding the stoma, forming a seal over the stoma. In a two-piece design, a wafer can be attached to the patient's skin (e.g., via a "peel and stick" adhesive backing), to form a fluid and air tight seal around the stoma and to provide an attachment site for an ostomy bag or pouch. Examples of ostomy devices that can be configured to divide stomal effluent into a solid fraction and a liquid fraction as described herein include, without limitation, those ostomy devices described in Published International Patent Application No. WO2010/030426, Published International Patent Application No. WO2010/060115, U.S. Patent Application Publication No. 2011/0028924, U.S. Patent Application Publication No. 2011/0092929, U.S. Patent Application Publication No. 2011/0040270, U.S. Pat. No. 5,947,941, or U.S. Pat. No. 4,834,731.

Figure 1:
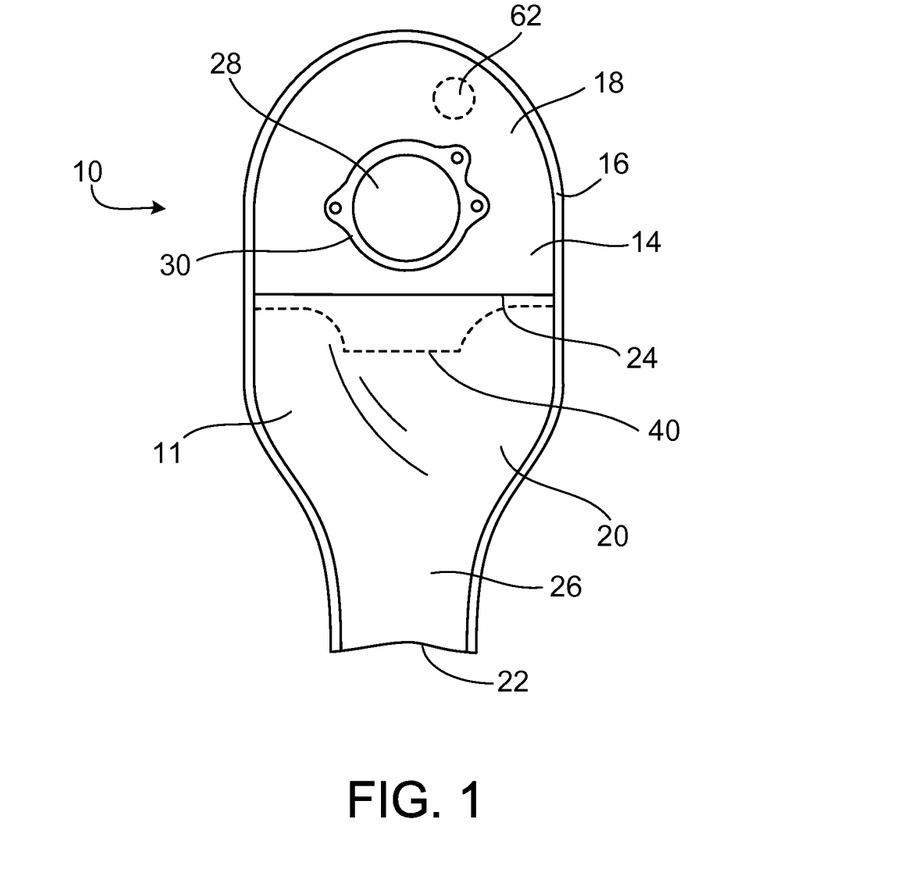
FIG. 1 is a front view of an ostomy device, in accordance with one embodiment provided herein.
Figure 2:
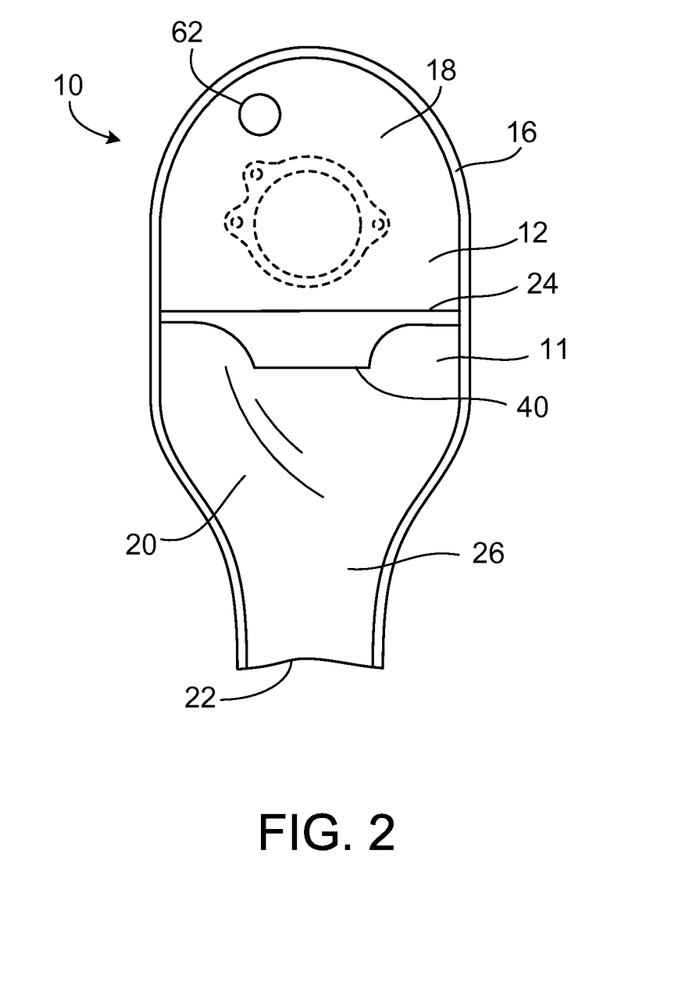
FIG. 2 is a rear view of the ostomy device of FIG. 1.

With reference to FIGS. 1 and 2, ostomy device 10 can be configured to include a pouch portion 11 having a front wall 12 that faces away from the body (e.g., abdomen) and a rear wall 14 that confronts the body (e.g., abdomen). Front wall 12 and rear wall 14 can be sealed together along a rim 16 by a peripheral thermoweld or other sealing means typical for such production. In some cases, a side wall (not shown) can be included to connect front wall 12 to rear wall 14 and to provide additional depth to pouch portion 11. The side wall could be constructed of a separate material or piece of material or materials that is sealed to front wall 12 and rear wall 14 in an appropriate manner, or could be integral to front wall 12 or rear wall 14.

Pouch portion 11 can be any desired shape such as regular shapes (e.g., square or elliptical shapes) or irregular shapes. Pouch portion 11 can be made of any suitable material or combination of materials. For example, pouch portion 11 can be made of one or more materials that are light weight, gas impermeable (e.g., air and fluid tight), flexible, expandable, and sound dampening such as polymeric plastic. In some cases, one or more layers of a thermoplastic material or a polymeric material (e.g., a polyvinyl chloride, low-density polyethylene, polyurethane, polyester, or polyamide film), one or more layers of a laminate (e.g., a laminate of one or more layers of ethylene vinyl acetate (EVA) and one or more layers of a gas barrier material such as poly(vinylidene chloride) (PVDC) or poly(vinylidene fluoride) (PVDF)), or a combination thereof can be used to make pouch portion 11.

In some cases, a comfort layer (not shown) can be added outside front wall 12 or rear wall 14. A comfort layer can be a soft layer that is permeable or impermeable to gas and liquid. A comfort layer can be made of any appropriate material or combination of materials. For example, a comfort layer can be made of nylon, polyethylene, polyester, viscose, rayon, or a combination thereof (e.g., a combination of polyester, viscose, and rayon).

With further reference to FIGS. 1 and 2, pouch portion 11 of ostomy device 10 can include a top region 18 and a bottom region 20 with a reclosable drain opening 22. Bottom region 20 can include a narrowed drain chute 26 leading to reclosable drain opening 22. Top region 18 and bottom region 20 can be partitioned by a filtering component 24. Filtering component 24 can include a screen or a membrane.

In some cases, filtering component 24 can be a size exclusion filter. In some cases, filtering component 24 can be a partially permeable membrane, a semi-permeable membrane, or a slightly porous membrane. In some cases, filtering component 24 can be a macrofilter. In some cases, filtering component 24 can be a filter made from one or more polymers. Examples of polymers that can be used to make a filtering component include, without limitation, polysulfone, polyethersulfone, polypropylene, polyvinylidene fluoride, polyolefin, polyester, polytetrafluoroethylene, and nylon. In some cases, filtering component 24 can be a filter made from nitrocellulose, cellulose acetate, textile fibers, or any appropriate combination of natural or synthetic materials.

In some cases, filtering component 24 can be designed to include any appropriate pore size to partition stomal effluent into a solid fraction and a liquid fraction. For example, such pore sizes can range from about 0.5 micrometers to about 1000 micrometers (e.g., from about 1 micron to about 1000 microns, from about 5 microns to about 1000 microns, from about 10 microns to about 1000 microns, from about 20 microns to about 1000 microns, from about 0.5 microns to about 800 microns, from about 0.5 microns to about 600 microns, from about 0.5 microns to about 500 microns, from about 10 microns to about 750 microns, or from about 50 microns to about 500 microns). In some cases, the pore size can be about 0.5, 1, 5, 10, 15, 25, 50, 100, 200, 500, or 1000 microns. In some cases, filtering component 24 can include a pore size distribution that allows a suitable collection efficiency to retain desired particulates in the solid fraction. In some cases, filtering component 24 can be designed to have pores that range in size from about 0.5 millimeters to about 5 millimeters (e.g., about 0.5 millimeters to about 4 millimeters, about 0.5 millimeters to about 3 millimeters, about 0.5 millimeters to about 2 millimeters, about 0.5 millimeters to about 1 millimeter, about 1 millimeter to about 1.5 millimeters, about 1 millimeter to about 2 millimeters, about 1 millimeter to about 2.5 millimeters, or about 0.75 millimeter to about 1.5 millimeters).

Figure 3:
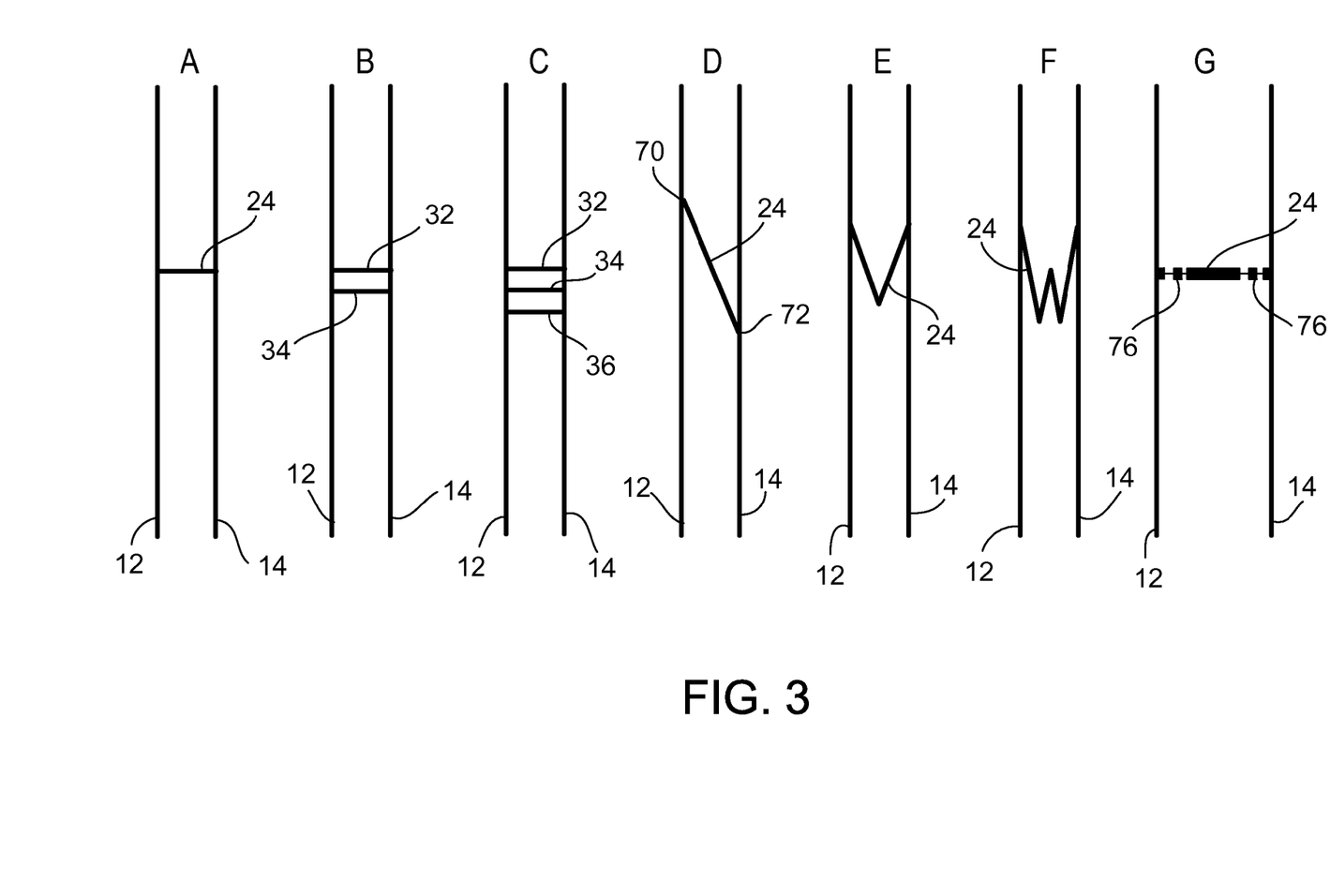
FIGS. 3A-G are side views of a filtering component of an ostomy pouch with single (FIG. 3A), double (FIG. 3B), or more (FIG. 3C) filtering components and exemplary filtering component attachment configurations (FIGS. 3D-3G), in accordance with some embodiments.

In some cases, filtering component 24 can include one or more filter layers. Such filter layers can be composed of the same or different filter materials with the same or different effective pore sizes. For example, in some cases, a first filter layer can retain large particulates, with a subsequent filter layer or layers retaining smaller particulates and/or odors from the liquid fraction. With reference to FIG. 3B, filtering component 24 can include a first filter layer 32 and a second filter layer 34. In some cases, first filter layer 32 can include a filter or an aggregate material with a larger effective pore size than second filter layer 34. In some cases, second filter layer 34 can include an effective pore size of about 0.5 microns. In some cases, second filter layer 34 can be used to minimize odors in the liquid fraction. In some cases, first filter layer 32 and second filter layer 34 can include filters of equivalent or substantially equivalent effective pore sizes, though any effective configuration of filters and pore sizes could be used (e.g., pore sizes from about 1 micron to about 1000 microns, pore sizes from about 5 microns to about 1000 microns, pore sizes from about 10 microns to about 1000 microns, pore sizes from about 20 microns to about 1000 microns, pore sizes from about 0.5 microns to about 800 microns, pore sizes from about 0.5 microns to about 600 microns, pore sizes from about 0.5 microns to about 500 microns, pore sizes from about 10 microns to about 750 microns, or pore sizes from about 50 microns to about 500 microns).

With reference to FIG. 3C, filtering component 24 can include a first filter layer 32, a second filter layer 34, and an additional filter layer or layers 36. In some cases, first filter layer 32 can be composed of a filter or an aggregate material with a larger effective pore size than second filter layer 34 or additional filter layer or layers 36. In some cases, second filter layer 32 can be composed of a filter or an aggregate material with a larger effective pore size than additional filter layer or layers 36. In some cases, additional filter layer or layers 36 can include an effective pore size of about 0.5 microns, though any effective configuration of filter layers and pore sizes could be used (e.g., pore sizes from about 1 micron to about 1000 microns, pore sizes from about 5 microns to about 1000 microns, pore sizes from about 10 microns to about 1000 microns, pore sizes from about 20 microns to about 1000 microns, pore sizes from about 0.5 microns to about 800 microns, pore sizes from about 0.5 microns to about 600 microns, pore sizes from about 0.5 microns to about 500 microns, pore sizes from about 10 microns to about 750 microns, or pore sizes from about 50 microns to about 500 microns). Any appropriate distance can be used between filter layers. For example, in some cases, first filter layer 32 and second filter layer 34 could be separate and distinct layers. In some cases, first filter layer 32 and second filter layer 34 could be spatially indistinct or part of a single unit.

With reference to FIG. 3D, in some cases, filtering component 24 can include a first filter attachment point 70 and a second filter attachment point 72 that configure filtering component 24 in a non-perpendicular orientation relative to front wall 12 and rear wall 14. In some cases, filtering component 24 can include material that is overlapped, folded, or pleated to increase filter surface area. For example, with reference to FIGS. 3E and 3F, filtering component 24 can include a single pleat or more than one pleat or fold.

Filtering component 24 can be attached to pouch 10 in any appropriate manner. For example, in some cases, filtering component 24 can be attached by heat sealing, or can be bonded, glued, or fastened to one or both of front wall 12 and rear wall 14. With reference to FIG. 3G, filtering component 24 can be suspended from an intermediate material 76 and not directly attached to front wall 12 and/or rear wall 14. Filtering component 24 can be attached to intermediate material 76 by thermoweld, adhesive, or any other effective fastening techniques or mechanisms. Intermediate material 76 can include any appropriate material or combination of materials. For example, in some cases, intermediate material 76 can include the same composition as front wall 12 and/or rear wall 14. In some cases, intermediate material can be composed of a material or combination of materials that is different from either or both front wall 12 and rear wall 14.

In some cases, filtering component 24 can divide pouch portion 11 such that top region 18 and bottom region 20 have equal or unequal proportions of pouch portion 11. For example, in some cases, a filter can divide pouch portion 11 such that top region 18 makes up about 10, 15, 25, 30, 40, 50, 60, or 70 percent of the total volume of pouch portion 11. Filtering component 24 can partition waste material collected in pouch portion 11 into a solid fraction and a liquid fraction. The liquid fraction is that fraction which can pass through filtering component 24 and which generally can be found in bottom region 20, especially when pouch portion 11 is oriented in an upright position. In some cases, the liquid fraction can include solid particulates sized to pass through filtering component 24. In some cases, the liquid fraction can include from about 0 to about 50 percent solid material in particulate form. For example, in some cases, a liquid fraction can contain from 0 up to about 5, 10, 15, 20, 25, 30, 40, or 50 percent solid material in particulate form.

With further reference to FIGS. 1 and 2, in some cases, pouch portion 11 can optionally include a second reclosable drain opening 40. Inclusion of an optional second reclosable drain opening 40 can allow top region 18 to be emptied as a separate compartment from bottom region 20. In some cases, second reclosable drain opening 40 can be constructed as part of front wall 12 or rear wall 14. Any appropriate closure system can be used to seal reclosable drain opening 22 or second reclosable drain opening 40 while a pouch device provided herein is being used to collect waste material. In some cases, a non-integral folding system, a non-integral clamp-style system, or other type of non-integral closure system can be used. In some cases, an integrated closure system can be used. For example, an ostomy device provided herein can be configured to include a closure system such as one of those described in U.S. Pat. Nos. 3,825,005, 4,403,991, 4,755,177, 5,125,133, or 6,544,241. The closure system used to seal second reclosable drain opening 40 can be either the same or different than the closure system used to seal reclosable drain opening 22.

In some cases, front wall 12 and rear wall 14 can be generally coterminous. In some cases, one of front wall 12 or rear wall 14 can project beyond the peripheral edge of the other, such that drain opening 22 is defined by, or between, stepped walls. In some cases, drain opening 22 or a second drain opening 40 can be provided as a slit in one of front wall 12 or rear wall 14.

In some cases, an ostomy device 10 provided herein (e.g., ostomy device 10) can be disposable or reusable. For example, a user who wishes to dispose of an ostomy device or the pouch portion of an ostomy device when the solid fraction fills top region 18 or at the end of a period of use may elect to use a disposable ostomy device or a disposable pouch portion of an ostomy device. The term "disposable" as used herein refers to an ostomy device or pouch portion of an ostomy device that is disposed of after a single use. In some cases, a user can elect to use an ostomy device having a pouch portion that includes drain opening 22 and second drain opening 40 that permits the contents to be emptied and the pouch portion to be reused for a period of time. In some cases, part or all of pouch portion 11 can be flushable.

With further reference to FIGS. 1 and 2, ostomy device 10 can include an entrance aperture 28 through which waste material enters pouch portion 11. In some cases, entrance aperture 28 can be formed in rear wall 14 closer to top region 18 than to bottom region 20 of pouch portion 11. In some cases, an ostomy device provided herein can include an attachment component (not shown) for attaching a pouch portion of an ostomy device to a user. An example of an attachment component is an adhesive wafer for indirectly or directly attaching a pouch portion of an ostomy device to a surface (e.g., skin) where the collection will be accomplished. In some cases, an attachment component can include a coupling component (e.g., a flange provided around a stoma) for coupling an attachment component (e.g., an adhesive wafer) to a pouch portion of an ostomy device. In some cases, ostomy device 10 can include a coupling ring 30 that can mechanically attach to a mating piece of an attachment component or a mating piece of a coupling component of an attachment component.

As described herein, an ostomy device provided herein can be a one-piece or two-piece system. For example, in some cases, such as in one-piece ostomy systems, an adhesive wafer can be joined together with a pouch portion as a single unit. In some cases, such as in two-piece ostomy systems, a coupling component of an attachment component and a coupling ring of a pouch portion can be included. For example, an adhesive wafer provided around a stoma can include a flange. Pouch portion 11 can include a coupling ring 30 joined to an outside surface of rear wall 14 in any appropriate manner. Coupling ring 30 of pouch portion 11 can attach mechanically to a mating piece on a flange provided around a stoma. Coupling ring 30 can interlock with the flange in any appropriate manner such as a pressure fit snap or lock-ring mechanism. In some cases, an attachment component and pouch portion can be coupled via matching coupling rings or matching flanges, and an adhesive surface can engage with and seal against a flange area. Examples of other coupling systems that can be used in combination with an ostomy device provided herein include, without limitation, those described in International Patent Application Publication No. WO 93/18725, International Patent Application Publication No. WO 94/18919, International Patent Application Publication No. WO 91/01118, International Patent Application Publication No. WO 91/01119, International Patent Application Publication No. WO 00/30576, International Patent Application Publication No. WO 01/54632, International Patent Application Publication No. WO 2010/106039, U.S. Pat. No. 5,800,415, or U.S. Pat. No. 7,727,205.

In some cases, a wafer can be manufactured of pectin or other organic material and can be made available in pre-cut sizes or can be customized for an individual user. In some cases, an adhesive wafer can include a medical grade barrier adhesive capable of absorbing humidity such as perspiration. In some cases, a suitable adhesive can include one or more hydrocolloid or hydrogel materials. Adhesive surfaces of an ostomy device provided herein can be made from any appropriate medical grade barrier adhesive such as one or more of the adhesive formulations disclosed in U.S. Pat. Nos. 4,367,732, 4,451,490, 5,369,130, 5,051,259, 5,714, 225, 6,171,594, 6,303,700, 6,332,879, 6,451,883, or 6,437, 038. In some cases, a release sheet (not shown), formed of, for example, siliconized paper or a polymeric film such as polyethylene terephthalate, can be peeled away from a surface of an adhesive wafer prior to application to the peristomal skin surfaces of a wearer.

In some cases, pouch portion 11 can include a vent aperture 62 and a filter for venting and/or deodorizing flatus from an interior region of pouch portion 11 to the outside thereof. Vent aperture 62 can be of any appropriate shape. For example, vent aperture 62 can be provided in the form of one or more U-shaped, V-shaped, S-shaped, linear, or other shaped slits or circular, oval, or otherwise shaped holes or openings. A deodorizing filter can be mounted to communicate with vent aperture 62, for example, in front wall 12 or rear wall 14. Vent aperture 62 can be located at any appropriate position on pouch portion 11. For example, vent aperture 62 can be located in top region 18, at a position generally higher than entrance aperture 28 and shifted laterally with respect to entrance aperture 28 when pouch portion 11 is in its normal upright orientation.

A deodorizing filter can include a deodorant such as, for example, granular activated charcoal, fibrous activated charcoal, or the like. Deodorizing filters can be made of a variety of materials or layers of materials. For example, a laminate including a deodorizing layer, a breathable waterproof layer, and a porous material layer can be used. Some filters include a filter-protecting panel of thermoplastic film or other barrier material to protect the deodorizing filter from clogging. For example, a gas-permeable, liquid-impermeable membrane can be used to protect the filter. In some cases, a pouch portion can be provided with a tortuous path vent opening, with or without a deodorizing filter. In some cases, a pouch portion can be provided with openings in a pouch wall, covered with deodorizing filters. In some cases, a pouch portion can be provided with replaceable filters attached to the pouch portion by a series of sequentially peelable adhesive members. In some cases, a pouch portion can include a gas venting filter that either has had the filter permanently bonded to the pouch wall, such as by heat or impulse welding or, if a removable filter is employed, a filter mounting member can be permanently affixed to a pouch wall surrounding the vent opening. Examples of venting filters include, without limitation, those described in International Patent Application Publication No. WO 2004/004612, European Patent No. 0 868 892, U.S. Patent Application Publication No. 2010/0010460, U.S. Patent Application Publication No. 2010/0145291, U.S. Pat. No. 4,211,224, U.S. Pat. No. 7,604,622, U.S. Pat. No. 6,165,159, U.S. Pat. No. 5,468,235, U.S. Pat. No. 5,348,546, U.S. Pat. No. 5,690,623, U.S. Pat. No. 5,074,851, U.S. Pat. No. 5,167,650, U.S. Pat. No. 5,658,267, U.S. Pat. No. 5,401,264, or U.S. Pat. No. 6,709,421.

Figure 4A:
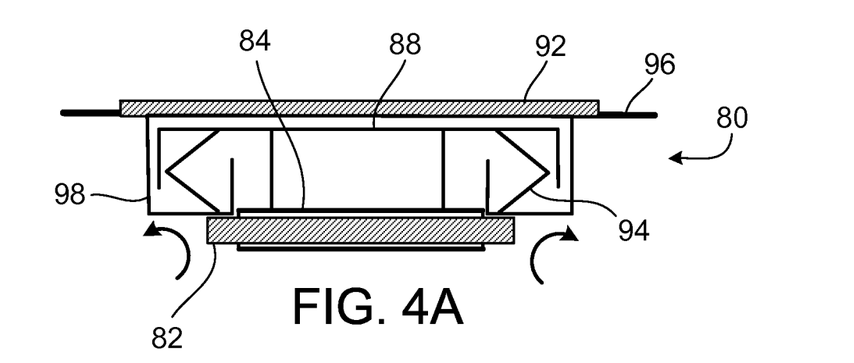
FIGS. 4A-B are side views of a user-actuated gas release valve in an un-actuated (FIG. 4A) and an actuated (FIG. 4B) configuration, in accordance with some embodiments.
Figure 4B:
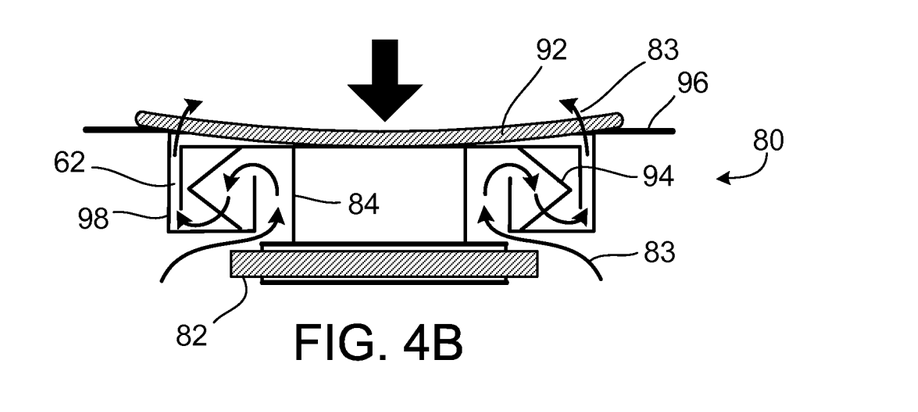

With reference to FIGS. 4A and 4B, in some cases, a vent aperture 62 can be controlled by a user-actuated valve assembly 80. Such a valve assembly can be selectively vented by a user at any time which is convenient for the user. Valve assembly 80 can be attached directly or indirectly to a pouch portion. In some cases, valve assembly 80 can be mounted to a pouch portion via a mount 96. Mount 96 can include a thermoweld, adhesive, laser weld, or any other appropriate attachment technique to permanently or removably attach valve assembly 80 to a pouch portion of an ostomy device. In some cases, valve assembly 80 can be mounted on a base that is mounted on a pouch portion. Valve assembly 80 can include a sealing member 82 that can be employed to seal vent aperture 62 when valve assembly 80 is closed (e.g., un-actuated), as shown in FIG. 4A. In some cases, sealing member 82 can be a gasket. Sealing member 82 can be constructed of any suitable material. For example, one or more materials such as rubber, synthetic rubber (e.g., EPDM), fluoropolymer elastomer, silicone, cork, felt, neoprene, nitrile rubber, fiberglass, polytetrafluoroethylene (PTFE), plastic polymers (e.g., polychlorotrifluoroethylen), or other suitable materials can be used.

Valve assembly 80 can include a valve housing 84. Valve housing 84 can be constructed of any suitable rigid or semi-rigid metal, plastic, or polymer material or combination of materials. Valve housing 84 can house a sealing member 82 and spring member 94. Spring member 94 can include one or more v-shaped springs, baffle systems, slowly released tension springs, or any other suitable spring-like mechanism. Spring member 94 can be biased so that it pulls sealing member 82 against valve seat 98 when at rest. Affixed or integral to valve housing 84 is push button 88 which compresses spring member 94 and forces sealing member 82 away from valve seat 98 when pressure (e.g., finger pressure) is applied as shown in FIG. 4B. This allows gas to pass through vent aperture 62, as indicated by arrows 83. Vented gas can also pass through a filter 92 before being released outside of a pouch portion. When push button 88 is released, the pressure of spring member 94 results in sealing member 82 being again seated against valve seat 98 and the vent aperture is closed off as shown in FIG. 4A. In some cases, valve assembly 80 can include a locking mechanism that when engaged, would maintain sealing member 82 in a position away from valve seat 98, which would allow continuous gas venting until the user disengaged the locking mechanism.

In operation of ostomy device 10, coupling flange 30 is engaged with a ring-shaped or other suitably shaped mating coupling flange (not shown) provided around the stoma. The coupling flange engagement forms a substantially leak-tight seal between pouch portion 11 and the stoma. Drain opening 22 of bottom compartment 20 is clamped shut in leak-tight fashion using any suitable known releasable closure means (not shown). In the illustrated embodiment, ostomy device 10 is intended as an ileostomy pouch for receiving semi-solid ileal effluent discharged from a user's ileal stoma. Semi-solid and gaseous waste material (not shown) are thus allowed to enter through entrance aperture 28 into top region 18 defined between front wall 12 and rear wall 14 of ostomy device 10. The semi-solid waste and gaseous waste can accumulate in top region 18 with the gaseous waste optionally being evacuated through a deodorizing filter and vent aperture 62. Liquid waste can advance through filtering component 24, and filtered liquid waste can accumulate in bottom region 20 while solid waste can be retained in top region 18. Accumulated liquid waste may be emptied by opening a releasable closure structure of drain opening 22 and allowing the liquid fraction to void. The releasable closure structure can then be closed to allow further waste accumulation.

Ostomy device 10 can contain multiple compartments that can independently be emptied through multiple drain openings and can operate in a similar fashion as a pouch with a single drain opening. The pouch portion can be attached to the user with an attachment wafer or other coupling structure in either a one-piece or two-piece system. Drain opening 22 of bottom compartment 20 can be clamped shut in leak-tight fashion using any suitable known releasable closure structure (not shown). The second drain opening 40 of top compartment 18 can also be clamped shut in leak-tight fashion using a suitable releasable closure structure (not shown). Semi-solid and gaseous waste material (not shown) can be allowed to enter through entrance aperture 28 into top region 18 defined between front wall 12 and rear wall 14 of ostomy device 10. Semi-solid waste and gaseous waste can accumulate in top region 18 with the gaseous waste optionally being evacuated through a deodorizing filter and vent aperture 62. Liquid waste can advance through filtering component 24, and filtered liquid waste can accumulate in bottom region 20 while solid waste can be retained in top region 18. Accumulated liquid waste can be drained from bottom region 20 by opening a releasable closure structure and allowing the liquid fraction to void. Solid waste retained in top region 18 can be emptied by opening a releasable closure structure of second drain opening 40. The releasable closure structures can then both be closed to allow further waste accumulation.

The materials and methods provided herein can be used by any appropriate ostomy patient or care provider. In some cases, patients or care providers of patients with ileostomy or colostomy can use an ostomy device provided herein. For example, ileostomy patients with stomal effluent that contains a relatively high volume of liquid and a relatively small amount of solid material can use an ostomy device provided herein to allow the liquid fraction to be disposed of separately from the solid fraction.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An ostomy device for collecting stomal effluent, wherein said ostomy device comprises a compartment having a front wall configured to face away from the body of a user and a back wall configured to confront said body of said user, and a partition located within said compartment and configured to extend from said front wall to said back wall, wherein said partition is liquid permeable and divides said compartment into at least a first compartment portion defined at least in part by a portion of said front wall, a portion of said back wall, and a first surface of said partition and at least a second compartment portion defined at least in part by a portion of said front wall, a portion of said back wall, and a second surface of said partition, wherein stomal effluent cannot pass from said first compartment portion to said second compartment portion without passing through said partition, wherein said partition prevents at least some solid waste from stomal effluent from passing from said first compartment portion to said second compartment portion, wherein said first compartment portion defines an opening for receiving stomal effluent from said user, wherein said second compartment portion defines a sealable opening for removing, from said ostomy device, at least some stomal effluent that passed from said first compartment portion to said second compartment portion through said partition.

2. The ostomy device of claim 1, wherein said partition comprises a filtering component.

3. The ostomy device of claim 1, wherein said partition further defines a sealable vent for releasing gas from said first compartment portion.

4. The ostomy device of claim 1, wherein said first compartment portion further defines a sealable opening for removing at least some solid waste from said ostomy device.

5. The ostomy device of claim 1, wherein said second compartment portion comprises a narrowed drain chute leading to said sealable opening.

6. A method for handling waste from a stoma, wherein said method comprises:
    (a) applying an ostomy device to said stoma, wherein said ostomy device comprises a front wall configured to face away from the body of a user, a back wall configured to confront said body of said user, a first compartment, a second compartment, and a partition located between said first compartment and said second compartment, configured to separate said first compartment from said second compartment, and configured to extend from said front wall to said back wall, wherein said first compartment is defined at least in part by a portion of said front wall, a portion of said back wall, and a first surface of said partition, wherein said second compartment is defined at least in part by a portion of said front wall, a portion of said back wall, and a second surface of said partition, wherein said partition is liquid permeable and permits at least some liquid waste from stomal effluent to pass through said partition from said first compartment to said second compartment, wherein stomal effluent cannot pass from said first compartment to said second compartment without passing through said partition, wherein said first compartment defines an opening for receiving stomal effluent from said user, and wherein said second compartment defines a sealable opening for removing at least some liquid waste from stromal effluent from said ostomy device, (b) allowing said ostomy device to be filled with stomal effluent, and (c) removing at least some liquid waste of stomal effluent from said second compartment through said sealable opening.

7. The method of claim 6, wherein at least some solid waste of stomal effluent is retained in said first compartment of said ostomy device.

8. The method of claim 6, wherein said first compartment further defines a sealable vent for releasing gas from said first compartment.

9. The method of claim 8, wherein said method comprises removing gas from said first compartment through said sealable vent.

10. The method of claim 8, wherein said partition comprises a pleat.

11. The method of claim 8, wherein said first compartment further defines a sealable opening for removing at least some solid waste of stomal effluent from said ostomy device.

12. The method of claim 8, wherein said second compartment comprises a narrowed drain chute leading to said sealable opening.

13. A method for partitioning a liquid fraction from a solid fraction of an ostomy effluent, wherein said method comprises:

(a) allowing stomal effluent to enter a first compartment of an ostomy device, wherein said ostomy device comprises a front wall configured to face away from the body of a user, a back wall configured to confront said body of said user, said first compartment, a second compartment, and a filter located between said first compartment and said second compartment, configured to separate said first compartment from said second compartment, and configured to extend from said front wall to said back wall, wherein said first compartment is defined at least in part by a portion of said front wall, a portion of said back wall, and a first surface of said filter, wherein said second compartment is defined at least in part by a portion of said front wall, a portion of said back wall, and a second surface of said filter, and wherein said second compartment defines a sealable opening for removing at least some liquid fraction from stomal effluent from said ostomy device and (b) allowing at least a portion of said ostomy effluent to pass through said filter to produce a substantially non-particulate fraction that is located in said second compartment, wherein said filter is liquid permeable, and wherein stomal effluent cannot pass from said first compartment to said second compartment without passing through said filter.

14. The method of claim 13, wherein said method comprises removing at least a portion of said substantially non-particulate fraction from said second compartment of said ostomy device through a sealable opening in said second compartment.

\* \* \* \* \*